United States Patent [19]
Dawson et al.

[11] Patent Number: 5,837,725
[45] Date of Patent: Nov. 17, 1998

[54] BRIDGED BICYCLIC AROMATIC COMPOUNDS AND THEIR USE IN MODULATING GENE EXPRESSION OF RETINOID RECEPTORS

[75] Inventors: Marcia I. Dawson, Menlo Park; James F. Cameron, Palo Alto; Peter D. Hobbs, Moss Beach; Ling Jong, Sunnyvale; Magnus Pfahl, Solana Beach; Xiao-kun Zhang, La Jolla; Jürgen M. Lehmann, Solana Beach, all of Calif.

[73] Assignees: SRI International, Menlo Park; La Jolla Cancer Research Foundation, La Jolla, both of Calif.

[21] Appl. No.: 448,991

[22] Filed: May 24, 1995

Related U.S. Application Data

[62] Division of Ser. No. 982,305, Nov. 25, 1992, Pat. No. 5,466,861.

[51] Int. Cl.$^6$ .......... A61K 31/335; A61K 31/38; C07D 317/00; C07D 339/02
[52] U.S. Cl. .......... 514/467; 514/440; 514/448; 514/433; 514/432; 514/456; 514/356; 514/337; 514/336; 514/569; 549/454; 549/398; 549/78; 549/71; 549/59; 549/39; 549/23; 546/326; 546/279.7; 546/281.7; 562/405; 562/490
[58] Field of Search .......... 549/454, 430, 549/453, 59, 35, 39, 71, 78, 22, 23, 398; 514/467, 440, 448, 433, 432, 456, 569, 356, 336, 337; 546/326, 279.7, 281.7; 562/405, 490

[56] References Cited

U.S. PATENT DOCUMENTS

| | | | |
|---|---|---|---|
| 4,808,631 | 2/1989 | Klaus | 514/561 |
| 4,826,969 | 5/1989 | Maignan et al. | 536/55.2 |
| 4,829,080 | 5/1989 | Maignan et al. | 514/432 |
| 4,833,240 | 5/1989 | Maignan et al. | 536/55.2 |
| 4,892,940 | 1/1990 | Maignan et al. | 536/55.2 |
| 5,023,363 | 6/1991 | Maignan et al. | 560/52 |
| 5,124,473 | 6/1992 | Shroot et al. | 560/56 |
| 5,387,594 | 2/1995 | Bernardon et al. | 514/346 |
| 5,391,766 | 2/1995 | Klaus et al. | 549/23 |
| 5,455,265 | 10/1995 | Chandraratna | 514/448 |

FOREIGN PATENT DOCUMENTS

| | | |
|---|---|---|
| 0718285 | 6/1996 | European Pat. Off. |
| 9311755 | 6/1993 | WIPO |
| WO 93/21146 | 10/1993 | WIPO |
| WO 94/15902 | 7/1994 | WIPO |
| 9605165 | 2/1996 | WIPO |

OTHER PUBLICATIONS

Graupner, G., et al., (1991) "6'-Substituted Naphthalene-2-Carboxylic Acid Analogs, A New Class Of Retinoic Acid Receptor Subtype-Specific Ligands", *Biochem. Biophys. Res. Commun.* 179(3): 1554–1561.

Heyman, R.A., et al., (1992) "9-cis Retinoic Acid Is A High Affinity Ligand For The Retinoid X Receptor", *Cell* 68: 397–406.

Pfahl et al., (1990) "Nuclear Retinoic Acid Receptors: Cloning, Analysis and Function", *Methods in Enzymology* 189: 256–270.

Zhang, X., et al., (1992) "Homodimer Formation Of Retinoid X Receptor Induced By 9-cis Retinoic Acid", *Nature* 358: 587–591.

Mandel, H., et al., in Goodman et al. *The Pharmacological Basis of Therapeutics*, Sixth Edition, MacMillan Publishing Co., Inc. (1980), pp. 1583–1592.

*Primary Examiner*—Deborah Lambkin
*Attorney, Agent, or Firm*—Dianne E. Reed; Bozicevic & Reed LLP

[57] ABSTRACT

Bridged bicyclic aromatic compounds are provided having the structure

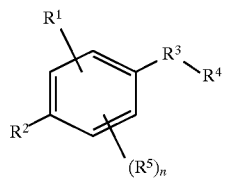

wherein $R^1$, $R^2$, $R^3$, $R^4$, $R^5$ and n are as defined herein. The novel compounds are useful for modulating gene expression of retinoic acid receptors, vitamin D receptors and thyroid receptors. Pharmaceutical compositions and methods for modulating gene expression are provided as well.

32 Claims, No Drawings

BRIDGED BICYCLIC AROMATIC COMPOUNDS AND THEIR USE IN MODULATING GENE EXPRESSION OF RETINOID RECEPTORS

This application is a divisional of U.S. patent application Ser. No. 07/982,305, filed Nov. 25, 1992, now U.S. Pat. No. 5,466,861.

TECHNICAL FIELD

This invention relates generally to the regulation of gene expression by retinoid receptors, and more particularly relates to novel bridged bicyclic aromatic compounds that are useful in modulating gene expression by retinoic acid receptors, retinoid X receptors, vitamin D receptors and thyroid receptors. The compounds are thus also useful for regulating cell differentiation processes controlled or regulated by retinoids, thyroid hormone, vitamin D, and/or 9-cis-retinoic acid. The invention additionally relates to pharmaceutical compositions and methods for treating mammalian individuals with the novel compounds.

BACKGROUND

Retinoids, which regulate cell differentiation by modulating gene expression and are thus able to reverse the preneoplastic transformation of cells, have excellent potential as therapeutic agents for the treatment and prophylaxis of cancer. See, e.g.: A. B. Roberts et al., "Cellular Biology and Biochemistry of Retinoids," in *The Retinoids*, vol. 2, eds. M. B. Sporn et al., Orlando: Academic Press, Inc., 1984, at pp. 209–286 (1984); and M. B. Sporn et al., "Biological Methods for Analysis and Assay of Retinoids," also in *The Retinoids*, vol. 2 (1984). Retinoids, particularly retinoic acid (RA) analogs, have been used in the treatment of leukemia, mycosis fungoides, basal cell carcinoma, and psoriasis and other hyperproliferative diseases of the skin (see R.C. Moon et al., "Retinoids and Cancer" in *The Retinoids*, vol. 2 (1984), supra). However, the systemic side effects of the compounds and their teratogenicity limit their utility. Side effects include, for example, bone remodeling, palmoplantar peeling, dermatitis, alopecia, hepatotoxicity, and systemic toxicity related as documented by H. Mayer et al., *Experientia* 34:1105 (1978) and by R. A. Pittsley et al., *New Eng. J. Med.* 308:1012 (1983).

The physiological activities of retinoids are mediated by two types of receptors, the retinoic acid receptors (RARs), and the retinoid X receptors (RXRs). RARs as well as several related receptors require heterodimerization with RXRs for effective DNA binding and function. However, in the presence of 9-cis-retinoic acid, a ligand for both RARs and RXRs, RXRs can also form homodimers. Compounds that selectively activate RXR homodimers have not yet been defined.

The present invention provides a new class of retinoids in the form of bridged bicyclic aromatic compounds as will be described in detail herein. These new compounds are useful for regulating and/or eliciting selective gene expression by receptors in the retinoic acid family, i.e., RARs, RXRs, vitamin D receptors (VDRs), and thyroid hormone receptors (THRs). While not wishing to be bound by theory, it is postulated that the presently disclosed and claimed compounds are effective in modulating gene expression by virtue of their capability of interacting with a receptor protein that binds to the aforementioned receptors. The compounds are also believed to be useful in modulating gene expression by inducing formation of RXR homodimers in addition to RAR-RXR, VDR-RXR and THR-RXR heterodimers.

The novel compounds are thus useful for controlling cellular processes that are regulated by retinoic acid, thyroid hormone, and/or vitamin D, as well as processes regulated by 9-cis-retinoic acid, the natural ligand for RXR. Thus, acne, leukemia, psoriasis, and skin aging, all of which are regulated by retinoic acid, may be treated using the compounds of the invention, as may bone calcification, regulated by vitamin D, and energy levels, regulated by thyroid hormone. Unlike the synthetic retinoids of the prior art, the present compounds are believed to provide for substantially reduced side effects and teratogenicity.

RELATED ART

The following references describe compounds which are structurally related to the compounds of the present invention:

U.S. Pat. No. 4,829,080 to Maignan et al. describes bridged, bicyclic aromatic compounds such as 4-(4,4-dimethyl-3,4-dihydro-6-benzopyranyl)carbonyl methyl benzoate and 4-(4,4-dimethyl-3,4-dihydro-6-benzopyranyl) carbonyl methyl benzoic acid (as the compounds are termed in the patent), for use in cosmetic compositions or pharmaceutical compositions for treating dermatologic diseases. The compounds are also stated to have anti-tumor activity.

U.S. Pat. No. 4,833,240 to Maignan et al. describes bridged, bicyclic aromatic compounds such as methyl(5,5,8,8-tetramethyl-5,6,7,8-tetrahydro-2-naphthyl)-4-carbonyl benzoate and methyl(5,5,8,8-tetramethyl-5,6,7,8-tetrahydro-2-naphthyl)-4-carbonyl benzoate (as the compounds are termed in the patent). As with the compounds of U.S. Pat. No. 4,829,080, these compounds are also stated to have anti-tumor activity and to be useful for treating dermatologic diseases.

U.S. Pat. No. 4,892,940 to Maignan et al. is similar to the above-mentioned patents in that bridged, bicyclic aromatic compounds are described which are stated to be useful in various medicinal and cosmetic compositions. Examples of the compounds encompassed by the generic structure defined in the patent include 2-methyl 6-(6,7-dimethyl-2-naphthyl)carbonyl naphthalene carboxylate and 6-(6,7-dimethyl-2-naphthyl) carbonyl-2-naphthalene carboxylic acid (as the compounds are termed in the patent).

U.S. Pat. Nos. 4,826,969 and 5,023,363 to Maignan et al. describe bridged aromatic compounds which contain a naphthalene structure. As with the compounds of the above-described patents, the compounds of these patents are stated to have anti-tumor activity and to be useful in the treatment of dermatologic diseases.

U.S. Pat. No. 4,808,631 to Klaus describes bridged aromatic compounds such as p-(5,6,7,8-tetrahydro-5,5,8,8-tetramethyl-2-naphthalenecarboxamido)benzoic acid as useful for treating inflammatory and rheumatic diseases.

G. Graupner et al., *Biochem. Biophys. Res. Commun.* 179(3):1554–1561 (1991), describe analogs of 6'-substituted naphthalene-2-carboxylic acid that elicit activation of the RARγ receptor but not of the RARα receptor.

R. A. Heyman et al., *Cell* 68:397–406 (1992), summarize experimental work that identifies 9-cis-retinoic acid as an RXR ligand.

X. -k. Zhang et al., *Nature* 358:587–591 (13 Aug. 1992), report that 9-cis-retinoic acid impacts on RXR homodimer formation, and propose a new mechanism for retinoid action.

The foregoing summaries are not intended as comprehensive statements of relevance; rather, the summaries are intended merely to identify subject matter in the various references that relates to that described and claimed herein. It should also be pointed out that none of the above-cited references disclose compounds such as those claimed herein, nor are methods provided for modulating gene expression by receptors in the retinoic acid family.

SUMMARY OF THE INVENTION

Accordingly, it is a primary object of the invention to address the above-mentioned need in the art by providing novel compounds useful to modulate gene expression by a receptor in the retinoic acid family of receptors.

It is another object of the invention to provide novel compounds useful to control cell differentiation processes regulated by retinoids, thyroid hormone, vitamin D, and/or 9-cis-retinoic acid.

It is still another object of the invention to provide novel compounds in the form of bridged, bicyclic aromatic structures.

It is yet another object of the invention to provide pharmaceutical compositions containing one or more of the novel compounds.

It is a further object of the invention to provide a method for modulating gene expression of a receptor selected from the group consisting of retinoic acid receptors, retinoid X receptors, vitamin D receptors, and thyroid receptors.

It is still a further object of the invention to provide a method for controlling cell differentiation processes regulated by retinoids, thyroid hormone, vitamin D, and/or 9-cis-retinoic acid.

Additional objects, advantages and novel features of the invention will be set forth in part in the description which follows, and in part will become apparent to those skilled in the art upon examination of the following, or may be learned by practice of the invention.

In one aspect, then, the invention relates to novel compounds having the structural formula (I)

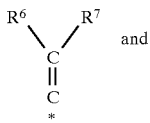

in which:

$R^1$ is selected from the group consisting of lower alkyl and adamantyl;

$R^2$ is O—$R^{13}$ or S—$R^{13}$ where $R^{13}$ is lower alkyl; or where $R^1$ is ortho to $R^2$, $R^1$ and $R^2$ may be linked together to form a 5- or 6-membered cycloalkylene ring, either unsubstituted or substituted with 1 to 4 lower alkyl groups, and optionally containing 1 or 2 heterocyclic atoms selected from the group consisting of O, S and NR where R is hydrogen or lower alkyl, preferably adjacent to the aromatic ring;

$R^3$ is selected from the group consisting of carbonyl,

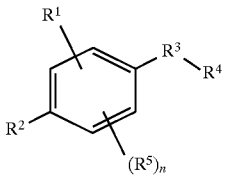

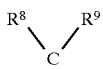

in which $X^1$ and $X^2$ are independently selected from the group consisting of O, S and methylene, wherein at least one of $X^1$ and $X^2$ is O or S, or wherein one of $X^1$ and $X^2$ is NR, and the other is methylene, m is 2 or 3, $R^6$, $R^7$, $R^8$ and $R^9$ are independently hydrogen or lower alkyl, with the proviso that when n is 0, $R^6$ and $R^7$ are not both hydrogen and $R^8$ and $R^9$ are not both hydrogen, or $R^8$ and $R^9$ may be linked together to form a cycloalkylene ring containing 3 to 6 carbon atoms, and * represents the point of attachment of the $R^3$ substituent to the remainder of the molecule; and $R^4$ is selected from the group consisting of

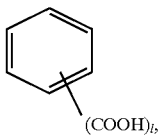

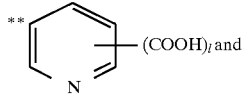

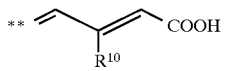

in which $R^{10}$ is hydrogen or methyl, l is 0 or 1, and ** represents the point of attachment of the $R^4$ substituent to the remainder of the molecule, the $R^5$ are independently selected from the group consisting of lower alkyl and lower alkoxy; and n is 0, 1, 2 or 3, with the proviso that if n is 0, $R^3$ is other than carbonyl, *C=CH$_2$ or CH$_2$.

The invention also encompasses pharmaceutically acceptable esters, amides and salts of such compounds, as will be explained in detail, infra.

In other aspects, the invention relates to pharmaceutical compositions containing the aforementioned compounds and to methods of using the compounds to modulate selective gene expression by a receptor in the retinoic acid family of receptors.

DETAILED DESCRIPTION OF THE INVENTION

Definitions and Nomenclature

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a bicyclic aromatic compound" includes mixtures of bicyclic aromatic compounds, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms. The term "cycloalkyl" intends a cyclic alkyl group of three to eight, preferably five or six, carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "alkylene" as used herein refers to a difunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like. "Lower alkylene" refers to an alkylene group of 1 to 6, more preferably 1 to 4, carbon atoms. The term "cycloalkylene" as used herein refers to a cyclic alkylene group, typically a 5- or 6-membered ring.

The term "alkene" as used herein intends a mono-unsaturated or di-unsaturated hydrocarbon group of 2 to 24 carbon atoms. Preferred groups within this class contain 2 to 12 carbon atoms. Asymmetric structures such as (AB)C=C(CD) are intended to include both the E and Z isomers. This may be presumed in structural formulae herein wherein an asymmetric alkene is present, or it may be explicitly indicated by the bond symbol ⌇.

"Optional" or "optionally" means that the subsequently described event or circumstance may or may not occur, and that the description includes instances where said event or circumstance occurs and instances where it does not. For example, the phrase "optionally substituted phenyl" means that the phenyl may or may not be substituted and that the description includes both unsubstituted phenyl and phenyl where there is substitution.

By the term "effective amount" of a compound as provided herein is meant a nontoxic but sufficient amount of the compound to provide the desired regulation of gene expression. As will be pointed out below, the exact amount required will vary from subject to subject, depending on the species, age, and general condition of the subject, the severity of the disease that is being treated, the particular bicyclic compound used, its mode of administration, and the like. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual along with the selected bicyclic compound without causing any undesirable biological effects or interacting in a deleterious manner with any of the other components of the pharmaceutical composition in which it is contained.

"Eliciting," "modulating" or "regulating" selective gene expression is intended to mean that a compound is capable of acting as an activator or an antagonist of gene expression by a particular receptor, i.e., a receptor in the retinoic acid family.

The "retinoic acid family" of receptors, also termed "retinoid receptors," is intended to encompass retinoic acid receptors, retinoid X receptors, vitamin D receptors and thyroid hormone receptors. The aforementioned three groups of receptors may also be loosely referred to herein as "retinoic acid receptors," i.e., such that the term includes retinoid X receptors, vitamin D receptors and thyroid hormone receptors in addition to retinoic acid receptors themselves.

"Bridged, bicyclic aromatic compounds" as used herein intends all compounds encompassed by the generic molecular structure of formula (I). These compounds may also be termed "retinoids."

The Novel Compounds

The novel compounds provided herein are those defined by structural formula (I) above. Preferred compounds within this generic structure include

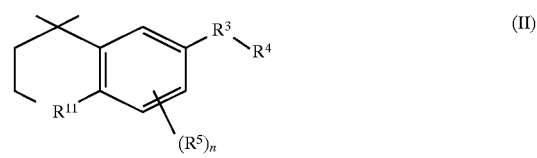

(II)

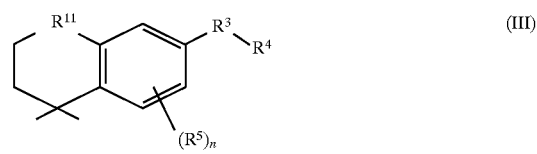

(III)

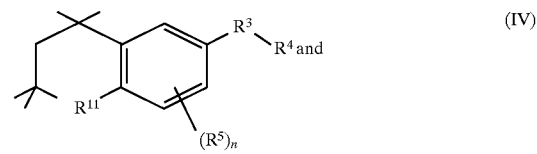

(IV)

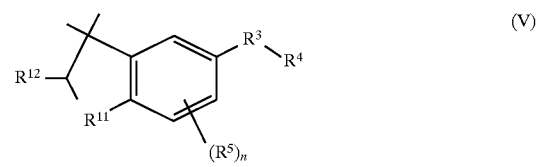

(V)

where $R^{11}$ is selected from the group consisting of O, S, (CH$_3$)$_2$C and CH$_2$, and $R^{12}$ is hydrogen or methyl. Particularly preferred compounds within this group are as shown in structural formula (II).

Preferred $R^3$ substituents, when $R^3$ has the general structure

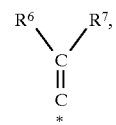

are selected from the group consisting of
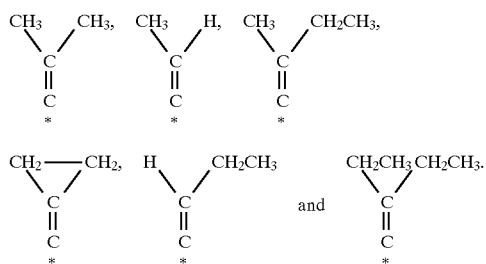
Preferred $R^3$ substituents, when $R^3$ has the general structure
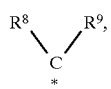
are selected from the group consisting of
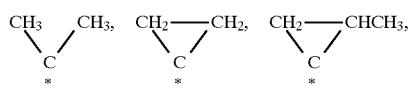
and
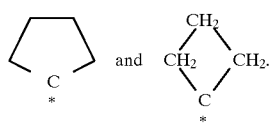
Examples of preferred structures encompassed by formula (II) thus include
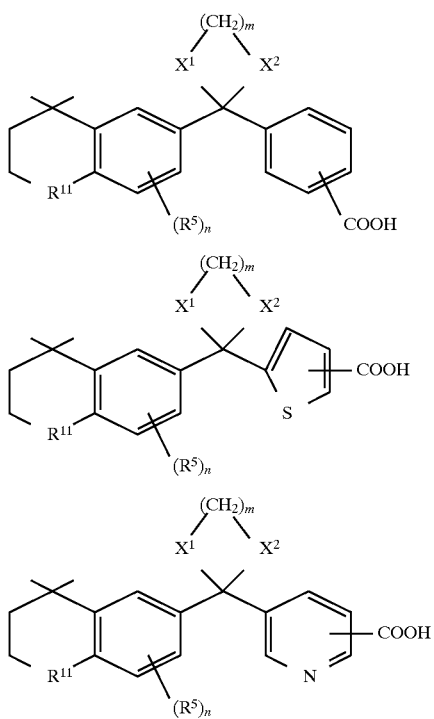
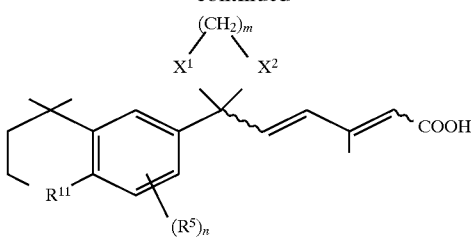
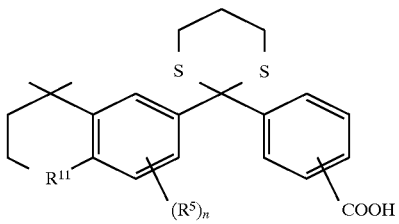
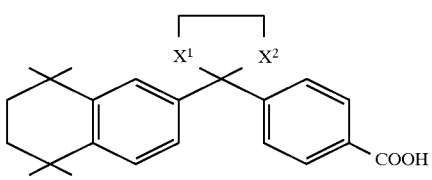
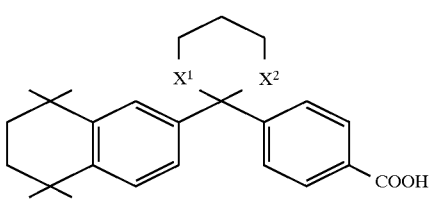
Examples of specific and particularly preferred compounds within the class of compounds defined by formula (II) include:
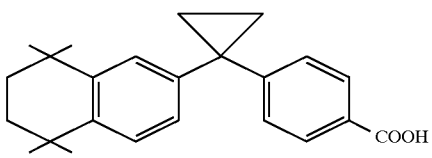
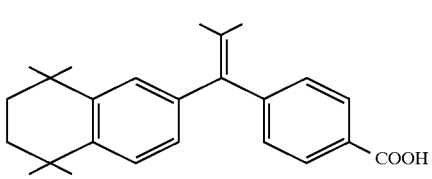
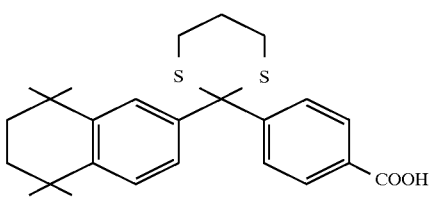

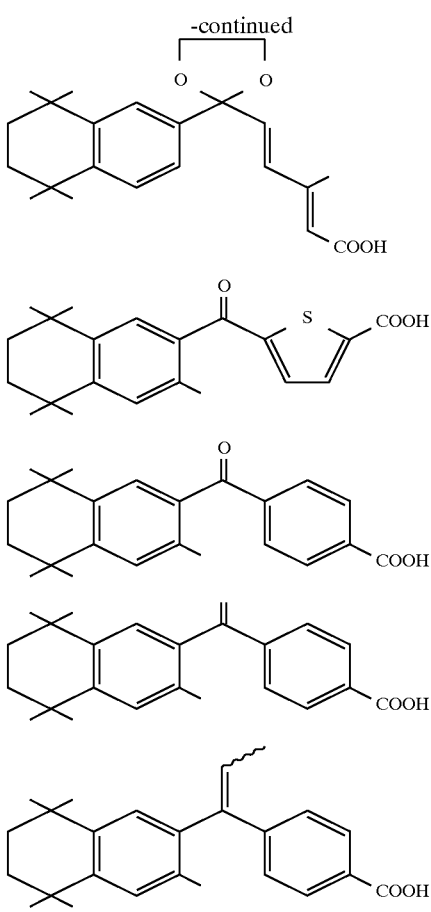

The invention also encompasses pharmaceutically acceptable nontoxic ester, amide and salt derivatives of those compounds of formula (I) containing a carboxylic acid moiety.

Pharmaceutically acceptable salts are prepared by treating the free acid with an appropriate amount of pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of structural formula (I) to base used are chosen to provide the ratio desired for any particular salts. For preparing, for example, the ammonium salts of the free acid starting material—a particular preferred embodiment herein—the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used.

Ester derivatives are typically prepared as precursors to the acid form of the compounds—as illustrated in the Examples below—and accordingly may serve as prodrugs. Generally, these derivatives will be lower alkyl esters such as acetate, propionate, and the like. Amide derivatives —(CO)NH$_2$, —(CO)NHR and —(CO)NR$_2$, where R is lower alkyl, may be prepared by reaction of the carboxylic acid-containing compound with ammonia or a substituted amine (as illustrated in Example 5 below).

Synthetic Methods

The compounds of the invention may be readily synthesized using techniques generally known to synthetic organic chemists. Suitable experimental methods for making and derivatizing bridged bicyclic aromatic compounds are described, for example, in the Maignan et al. patents summarized above, the disclosures of which patents are hereby incorporated by reference. Methods for making specific and preferred compounds of the present invention are described in detail in Examples 1–14 below.

Utility and Administration

The compounds of the invention defined by structural formula (I), including the pharmacologically acceptable esters, amides or salts thereof, are useful to elicit and/or regulate selective gene expression by receptors in the retinoic acid family and to control cell differentiation processes regulated by retinoids, vitamin D and/or thyroid hormone. As noted above, the compounds of the invention are thus useful for treating acne, leukemia, psoriasis, skin aging, bone calcification and energy levels, as well as other indications related to cellular processes regulated by retinoic acid, vitamin D, thyroid hormone and 9-cis-retinoic acid.

The compounds of the invention may be conveniently formulated into pharmaceutical compositions composed of one or more of the compounds in association with a pharmaceutically acceptable carrier. See, e.g., *Remington's Pharmaceutical Sciences*, latest edition, by E. W. Martin (Mack Publ. Co., Easton Pa.) discloses typical carriers and conventional methods of preparing pharmaceutical compositions that may be used in conjunction with the preparation of formulations of the inventive compounds.

The compounds may be administered orally, parenterally (e.g., intravenously), by intramuscular injection, by intraperitoneal injection, topically, transdermally, or the like, although oral or topical administration is typically preferred. The amount of active compound administered will, of course, be dependent on the subject being treated, the subject's weight, the manner of administration and the judgment of the prescribing physician. Generally, however, dosage will approximate that which is typical for the administration of retinoic acid, and will preferably be in the range of about 2 μg/kg/day to 2 mg/kg/day.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Experimental

The following examples are put forth so as to provide those of ordinary skill in the art with a complete disclosure and description of how the compounds claimed herein are made and evaluated, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

In describing the location of groups and substituents, the following numbering system will be employed throughout the examples:

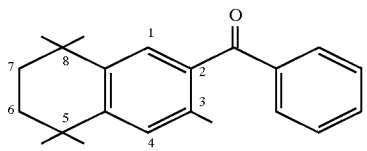

EXAMPLE 1

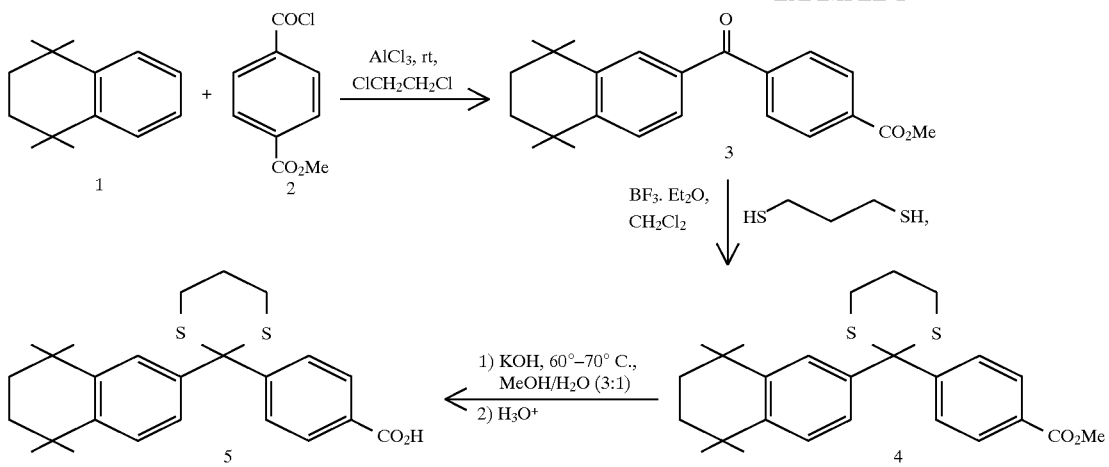

(a.) Methyl 4-[(5,6,7,8-tetrahydro-5,5,8,8-tetramethyl-2-naphthalenyl)carbonyl]benzoate (3):

To a suspension of aluminum chloride (1.13 g, 8.5 mmol) in 1.5 mL of 1,2-dichloroethane at 0° C. under argon was added a solution of 1,2,3,4-tetrahydro-1,1,4,4-tetramethylnaphthalene 1 (1.45 g, 7.7 mmol) (Kagechika, H., et al., *J. Med. Chem.* 31:2182 (1988)) and 4-carbomethoxybenzoyl chloride 2 (1.56 g, 7.9 mmol) (4-carbomethoxybenzoyl chloride 2 was obtained from mono-methyl terephthalate, which is readily available from Aldrich, in one step ($SOCl_2$, DMF)) in 6 mL of 1,2-dichloroethane. The resulting solution was brought to room temperature and stirred thereafter for 16 h. The reaction mixture was poured onto ice water and extracted with 40% ethyl acetate/hexane. The combined organic layers were washed with saturated aqueous $NaHCO_3$ and brine. The solution was dried over anhydrous $MgSO_4$, filtered and concentrated to afford an orange solid (4.5 g). Flash chromatography (50% dichloromethane/hexane) yielded the desired product 3 as a pale yellow solid (2.07 g). Recrystallization from dichloromethane/hexane afforded the desired product 3 as a white, crystalline solid (1.96 g, 50%): m.p. 146°–148° C.; $R_f$ 0.14 (50% $CH_2Cl_2$/hexane). The structure of the product was also confirmed using IR, $^1H$ NMR and mass spectroscopy.

(b.) [2(5,6,7,8-Tetrahydro-5,5,8,8-tetramethylnaphthalen-2-yl)-2-(4-carbomethoxyphenyl)]-1,3-dithiane (4):

To a solution of the keto-ester 3 (97 mg, 0.277 mmol) in 3 mL of chloroform at 0° C. under argon was added a solution of 1,3-propanedithiol (33 µL, 36 mg, 0.332 mmol) followed by boron trifluoride etherate (17 µL, 0.140 mmol). The resulting mixture was stirred at 0° C. for 1 h and then warmed to room temperature overnight. The reaction mixture was quenched by pouring into saturated aqueous $Na_2CO_3$, and extracted with dichloromethane. The combined organic layers were dried over anhydrous $MgSO_4$, filtered, and concentrated to afford a yellow solid (0.108 g). Recrystallization from ethyl acetate/hexane afforded the desired dithiane 4 as a white, crystalline solid (0.087 g, 71%): m.p. 195°–197° C.; $R_f$ 0.32 (50% $CH_2Cl_2$/hexane). The structure of the product was also confirmed using IR, $^1H$ NMR and mass spectroscopy.

(c.) [2-(5,6,7,8-Tetrahydro-5,5,8,8-tetramethylnaphthalen-2-yl)-2-(4-carboxyphenyl)]-1,3-dithiane (5):

To a suspension of the ester 4 (85 mg, 0.193 mmol) in 75% aqueous methanol (2 mL) was added 0.024 g of potassium hydroxide and the mixture was stirred at 50° C. for 2 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford a white solid. Recrystallization from benzene/hexane afforded the desired acid 5 as a white, powder (0.076 g, 92%): m.p. 229°–231° C. The structure of the product was also confirmed using IR, $^1H$ NMR and mass spectroscopy.

EXAMPLE 2

C. for 1 h and then warmed to room temperature overnight. The reaction mixture was quenched by pouring into saturated aqueous $Na_2CO_3$, and extracted with 40% ethyl acetate/hexane. The combined organic layers were dried over anhydrous $MgSO_4$, filtered, and concentrated to afford a solid. Flash chromatography (30; 40% $CH_2Cl_2$/hexane) yielded the desired dithiane 6 as a white solid (0.088 g, 90%): m.p. 105°–107° C.; $R_f$ 0.33 (50% $CH_2Cl_2$/hexane). The structure of the product was also confirmed using IR, $^1H$ NMR and mass spectroscopy.

(b.) [2-(5,6,7,8-Tetrahydro-5,5,8,8-tetramethyl-2-naphthalenyl)-2-(4-carboxyphenyl)]-1,3-dithiolane (7):

To a suspension of the ester 6 (85 mg, 0.199 mmol) in 75% aqueous methanol (3 mL) was added one pellet of potassium hydroxide (0.11 g) and the mixture was stirred at 70° C. for 1 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to

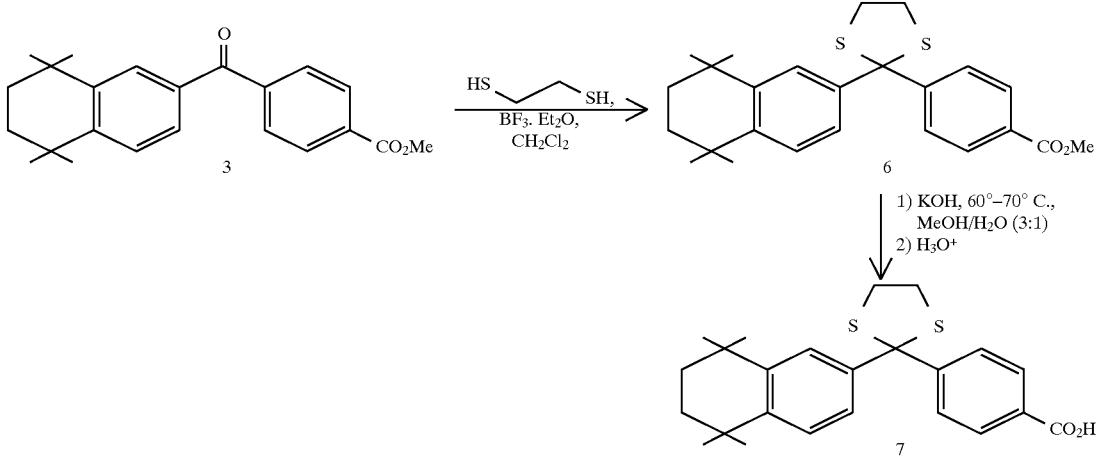

(a.) [2-(5,6,7,8-Tetrahydro-5,5,8,8-tetramethyl-2-naphthalenyl)-2-(4-carbomethoxyphenyl)]-1,3-dithiolane (6):

To a solution of the keto-ester 3 (80 mg, 0.228 mmol) in dichloromethane (2 mL) at 0° C. under argon was added a solution of ethanedithiol (26 mg, 0.27 mmol) in dichloromethane (0.5 mL) followed by boron trifluoride etherate (0.04 mL, 0.3 mmol). The resulting mixture was stirred at 0° afford a white solid. Recrystallization from dichloromethane-hexane afforded the desired acid 7 as a white powder (0.064 g, 79%): m.p. 218°–221° C. The structure of the product was also confirmed using IR, $^1H$ NMR and mass spectroscopy.

EXAMPLE 3

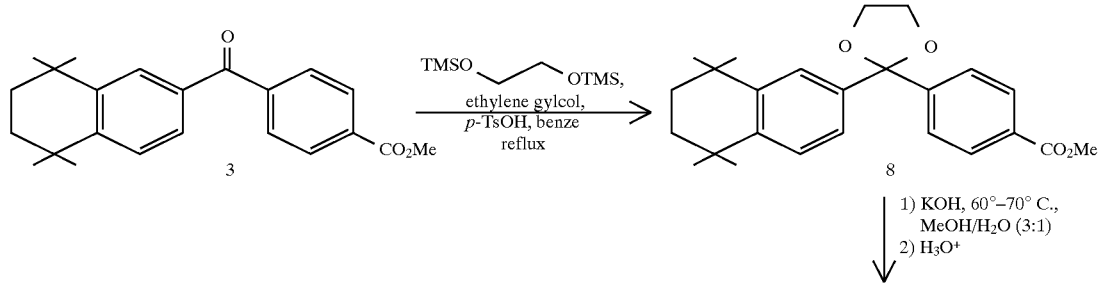

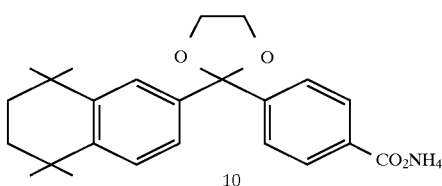

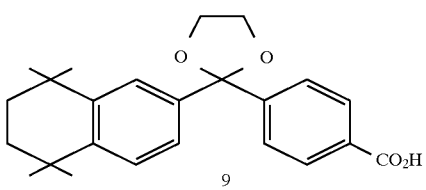

(a.) [2-(5,6,7,8-Tetrahydro-5,5,8,8-tetramethyl-2-naphthalenyl)-2-(4-carbomethoxyphenyl)]-1,3-dioxolane (8):

To a solution of keto-ester 3 (80 mg, 0.228) in 1 mL of benzene was added ethylene glycol (1 mL), 1,2-bis (trimethylsilyloxy)ethane (2 mL) and a catalytic amount of p-TsOH. The reaction mixture was heated at reflux for 4 h and then cooled to room temperature. The solution was poured into saturated aqueous $NaHCO_3$ and extracted with 40% ethyl acetate/hexane. The combined organic layers were dried over anhydrous $MgSO_4$, filtered, and concentrated to afford a solid. Flash chromatography (50% $CH_2Cl_2$/hexane) yielded the desired ketal 8 as a white solid (0.082 g, 91%): m.p. 145°–147° C.; $R_f$ 0.16 (50% $CH_2Cl_2$/hexane). The structure of the product was also confirmed using IR, $^1H$ NMR and mass spectroscopy.

(b.) [2-(5,6,7,8-Tetrahydro-5,5,8,8-tetramethyl-2-naphthalenyl)-2-(4-carboxyphenyl)]-1,3-dioxolane ammonium salt (10):

To a suspension of the ester 8 (50 mg, 0.127 mmol) in 75% aqueous methanol (2 mL) was added one pellet of potassium hydroxide (0.1 g), and the reaction mixture was stirred at 70° C. for 1 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford a white solid 9. The acid 9 was dissolved in dichloromethane (4 mL) under argon, and ammonia gas was condensed into the solution, which was stirred for 5 min at −33° C. The solution was warmed to room temperature for 20 min to evaporate the ammonia and concentrated to afford the ammonium salt 10 as a white powder (47 mg, 93%): m.p. 259°–261° C. The structure of the product was also confirmed using IR, $^1H$ NMR and mass spectroscopy.

EXAMPLE 4

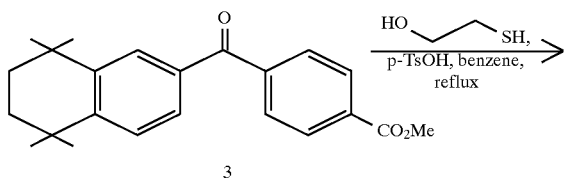

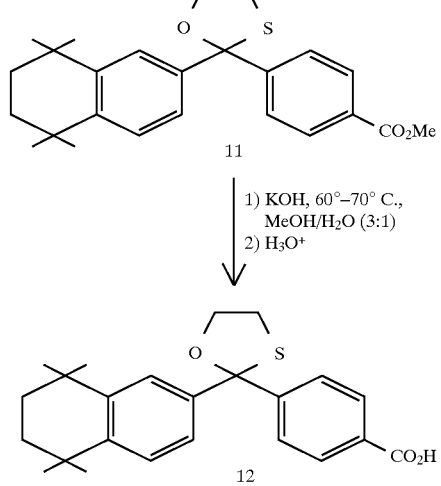

(a.) [2-(5,6,7,8-Tetrahydro-5,5,8,8-tetramethyl-2-naphthalenyl)-2-(4-carbomethoxyphenyl)]-1,3-oxathiolane (11):

To a solution of keto-ester 3 (88 mg, 0.251) in 2 ml of benzene was added 2-mercaptoethanol (1 mL), and a catalytic amount of p-TsOH. The reaction mixture was heated at reflux overnight and then cooled to room temperature. The solution was poured into saturated aqueous $NaHCO_3$ and extracted with 40% ethyl acetate/hexane. The combined organic layers were dried over anhydrous $MgSO_4$, filtered, and concentrated to afford a solid. Flash chromatography (50% $CH_2Cl_2$/hexane) yielded the desired ketal 11 as a white solid (0.09 g, 87%): m.p. 122°–124° C.; $R_f$ 0.24 (50% $CH_2Cl_2$/hexane). The structure of the product was also confirmed using IR, $^1H$ NMR and mass spectroscopy.

(b.) [2-(5,6,7,8-Tetrahydro-5,5,8,8-tetramethyl-2-naphthalenyl)-2-(4-carboxyphenyl)]-1,3-oxathiolane (12):

To a suspension of the ester 11 (64 mg, 0.156 mmol) in 75% aqueous methanol (3 mL) was added one pellet of potassium hydroxide (0.12 g), and the reaction mixture was stirred at 75° C. for 1 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford a white solid. Recrystallization from dichloromethane-hexane afford the desired acid 12 as a white powder (0.06 g, 97%): m.p. 216°–217.5° C. The structure of the product was also confirmed using IR, $^1H$ NMR and mass spectroscopy.

EXAMPLE 5

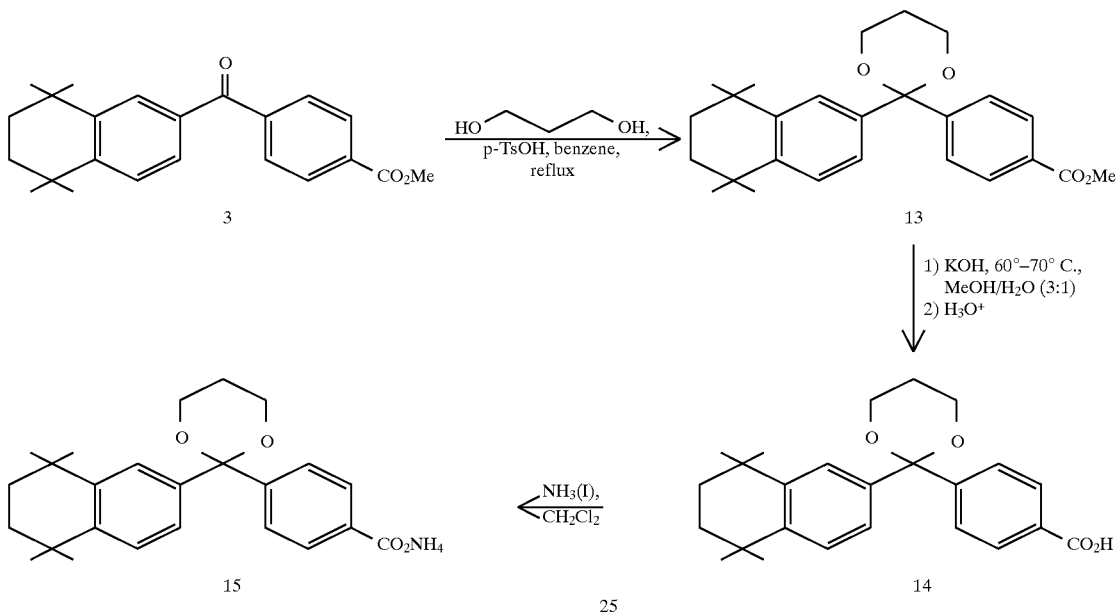

(a.) [2-(5,6,7,8-Tetrahydro-5,5,8,8-tetramethyl-2-naphthalenyl)-2-(4-carbomethoxyphenyl)]-1,3-dioxane (13):

To a solution of keto-ester 3 (150 mg, 0.428 mmol) in 5 ml of benzene was added 1,3-propanediol (1.5 mL), and a catalytic amount of p-TsOH. The reaction mixture was heated at reflux overnight and then cooled to room temperature. The solution was poured into saturated aqueous NaHCO$_3$ and extracted with 40% ethyl acetate/hexane. The combined organic layers were dried over anhydrous MgSO$_4$, filtered, and concentrated to afford a solid. Flash chromatography (50% CH$_2$Cl$_2$/hexane) yielded the desired ketal 13 as a white solid (0.164 g, 94%): m.p. 157°–159° C.; R$_f$ 0.24 (5% ethyl acetate/hexane). The structure of the product was also confirmed using IR, $^1$H NMR and mass spectroscopy.

(b.) [2-(5,6,7,8-Tetrahydro-5,5,8,8-tetramethyl-2-naphthalenyl)-2-(4-carboxyphenyl)]-1,3-dioxane ammonium salt (15):

To a suspension of the ester 13 (0.1 g, 0.245 mmol) in 75% aqueous methanol (3 mL) was added one pellet of potassium hydroxide (0.12 g). The reaction mixture was stirred at 80° C. for 30 min during which time the material dissolved. The solution was cooled to room temperature, acidified with 1N aqueous hydrochloric acid, and then extracted with 80% ethyl acetate/hexane. The combined organic layers were dried over anhydrous MgSO$_4$, filtered, and concentrated to afford a white solid 14. The acid 14 was dissolved in dichloromethane (4 mL) under argon. Ammonia gas was condensed into the flask and the mixture was stirred for 5 min at −33° C. The solution was warmed to room temperature for 20 min to evaporate ammonia and concentrated to afford the ammonium salt 15 as a white powder (0.238 g, 97%): m.p. 228°–230° C. The structure of the product was also confirmed using IR, $^1$H NMR and mass spectroscopy.

EXAMPLE 6

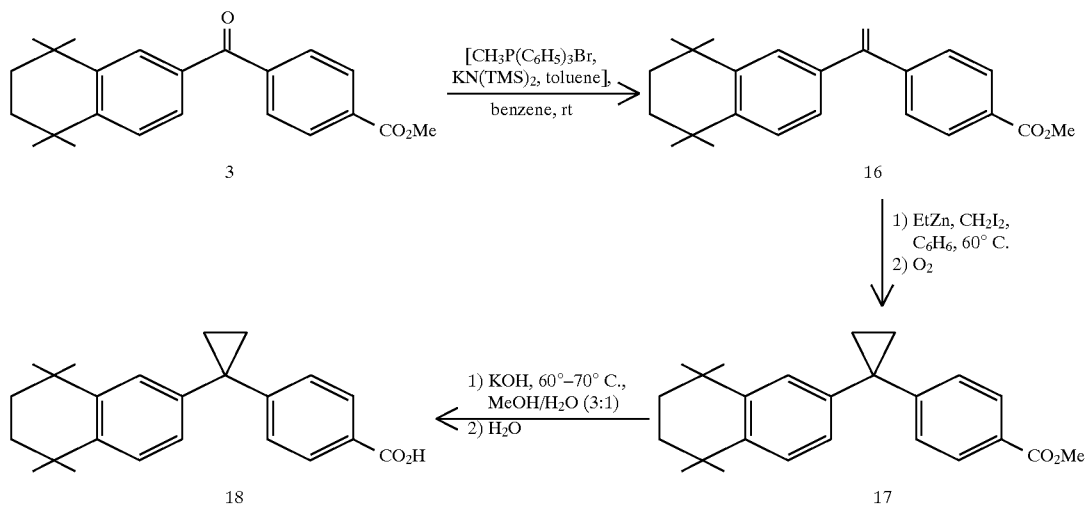

(a.) Methyl 4-[1-(5,6,7,8-tetrahydro-5,5,8,8-tetramethyl-2-naphthalenyl)-1-ethenyl]benzoate (16):

To a suspension of methyltriphenylphosphonium bromide (0.78 g, 2.18 mmol) in 5 mL of benzene under argon at room temperature was added a 0.5M solution of potassium hexamethyldisilazide in toluene (4.4 mL, 2.2 mmol), and the yellow solution was stirred for 5 min. A solution of keto-ester 3 (0.51 g, 1.455 mmol) in 7 mL of benzene was added, and the orange solution was stirred for 1 h at room temperature. The reaction mixture was poured into saturated aqueous $NaHCO_3$ and extracted with 40% ethyl acetate/hexane. The combined organic layers were dried over anhydrous $MgSO_4$, filtered through a plug of silica gel, and concentrated to afford a solid. Flash chromatography (30% dichloromethane/hexane) yielded the desired product 16 as a white solid (0.405 g, 80%): m.p. 117°–118° C.; $R_f$ 0.2 (25% $CH_2Cl_2$/hexane). The structure of the product was also confirmed using IR, $^1H$ NMR and mass spectroscopy.

(b.) [1-(5,6,7,8-Tetrahydro-5,5,8,8-tetramethyl-2-naphthalenyl)-1-(4-carbomethoxyphenyl)]cyclopropane (17):

To a solution of ethene 16 (0.130 g, 0.373 mmol) in 10 mL of benzene under argon at room temperature was added a 1M solution of diethylzinc in hexane (5.6 mL, 5.6 mmol), and the reaction mixture was heated to 60° C. Diiodomethane (0.48 mL, 6.0 mmol) in 2 mL of benzene was added dropwise for 5 min. The reaction mixture was cooled to room temperature and oxygen was bubbled through for 3 h. The cloudy solution was diluted with 40% ethyl acetate/hexane and washed with aqueous hydrochloric acid, water and saturated aqueous $NaHCO_3$. The organic layer was dried over anhydrous $MgSO_4$, filtered, and concentrated to afford a solid. Flash chromatography (30%; 40% $CH_2Cl_2$/hexane) yielded the desired product 17 as a white solid (0.08 g, 59%): m.p. 100°–102° C.; $R_f$ 0.36 (50% $CH_2Cl_2$/hexane). The structure of the product was also confirmed using IR, $^1H$ NMR and mass spectroscopy.

(c.) [1-(5,6,7,8-Tetrahydro-5,5,8,8-tetramethyl-2-naphthalenyl)-1-(4-carboxyphenyl)]cyclopropane (18):

To a suspension of the ester 17 (60 mg, 0.166 mmol) in 75% aqueous methanol (2 mL) was added one pellet of potassium hydroxide (0.12 g), and the reaction mixture was stirred at 70° C. for 1 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford a white solid. Recrystallization from dichloromethane-hexane afforded the desired acid 18 as a white powder (0.055 g, 95%): m.p. 333°–335° C. The structure of the product was also confirmed using IR, $^1H$ NMR and mass spectroscopy.

EXAMPLE 7

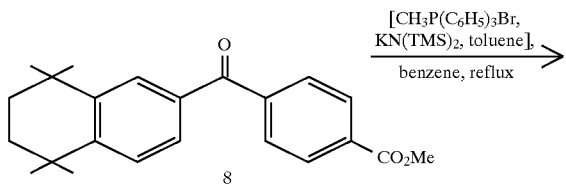

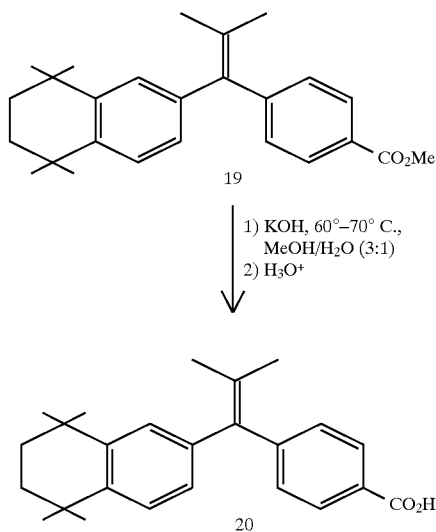

(a.) Methyl 4-[1-(5,6,7,8-tetrahydro-5,5,8,8-tetramethyl-2-naphthalenyl)-2-methyl-1-propenyl]benzoate (19):

To a suspension of isopropyltriphenylphosphonium iodide (0.35 g, 0.807 mmol) in 3 mL of benzene under argon at room temperature was added a 0.5M solution of potassium hexamethyldisilazide in toluene (1.8 mL, 0.89 mmol), and the red solution was stirred for 5 min. A solution of keto-ester 3 (0.169 g, 0.481 mmol) in 3 mL of benzene was added, and the red solution was heated to 110° C., while approximately 4 mL of benzene was distilled out. After 1 h, the reaction mixture was diluted with 40% ethyl acetate/hexane and washed with saturated aqueous $NaHCO_3$ and brine. The organic layer was dried over anhydrous $MgSO_4$, filtered through a plug of silica gel, and concentrated to afford a solid. Flash chromatography (40% dichloromethane/hexane) yielded the desired product 19 as a white powder (0.128 g, 71%): $R_f$ 0.44 (50% $CH_2Cl_2$/hexane). The structure of the product was also confirmed using IR, $^1H$ NMR and mass spectroscopy.

(b.) 4-[1-(5,6,7,8-Tetrahydro-5,5,8,8-tetramethyl-2-naphthalenyl)-2-methyl-1-propenyl]benzoic acid (20):

To a suspension of the ester 19 (0.115 g, 0.304 mmol) in 75% aqueous methanol (3 mL) was added one pellet of potassium hydroxide (0.12 g), The mixture was stirred at 75° C. for 1 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford the desired acid 20 as a white powder (0.11 g, 99%): m.p. 204°–206° C. The structure of the product was also confirmed using IR, $^1H$ NMR and mass spectroscopy.

EXAMPLE 8

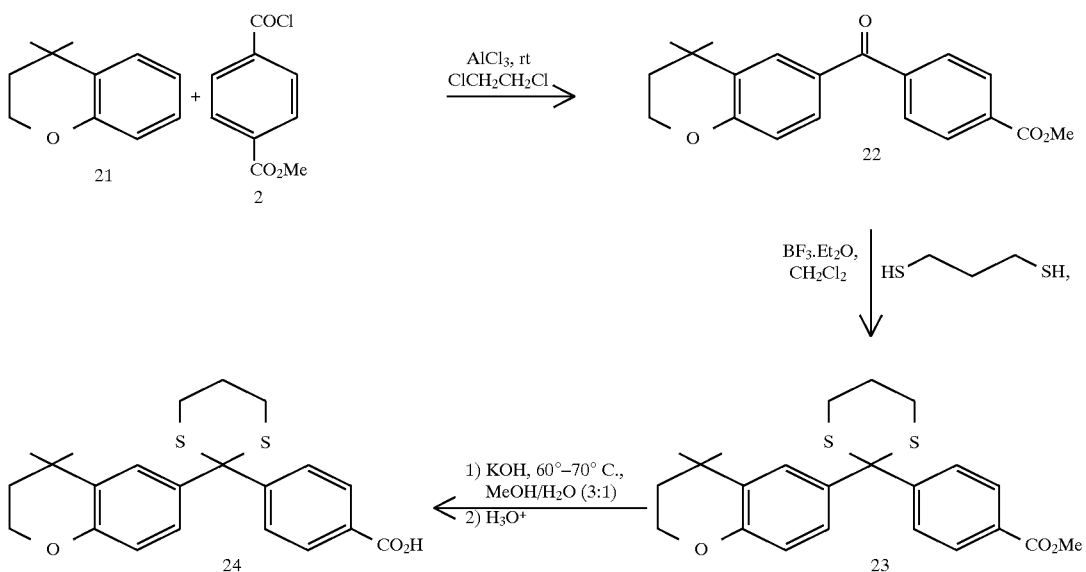

(a.) Methyl 4-[(4,4-dimethyl-3,4-dihydro-2H-1-benzopyran-6-yl)carbonyl]benzoate (22) (Maignan, J., et al., BE 1,000,195):

To a suspension of aluminum chloride (1.6 g, 12 mmol) in 1 mL of 1,2-dichloroethane under argon at room temperature was added a solution of 4,4-dimethyl-3,4-dihydro-2H-1-benzopyran 21 (1.5 g, 9.25 mmol) (Dawson, M. I., et al., *J. Med. Chem.* 27:1516–1531 (1984)) and 4-carbomethoxybenzoyl chloride 2 (1.79 g, 9 mmol) in 9 mL of 1,2-dichloroethane. The reaction mixture was stirred overnight, poured onto ice-water and extracted with 40% ethyl acetate/hexane. The combined organic layers were washed with saturated aqueous $NaHCO_3$ and brine. The solution was dried over anhydrous $MgSO_4$, filtered, and concentrated to afford a yellow solid (3.24 g). Flash chromatography (80% dichloromethane/hexane) yielded the desired product 22 as a white powder (1.42 g, 49%): m.p. 129°–131° C.; $R_f$ 0.26 ($CH_2Cl_2$). The structure of the product was also confirmed using IR, $^1H$ NMR and mass spectroscopy.

(b.) [2-(4,4-Dimethyl-3,4-dihydro-2H-1-benzopyran-6-yl)-2-(4-carbomethoxyphenyl)]-1,3-dithiane (23):

To a solution of the keto-ester 22 (0.152 g, 0.469 mmol) in dichloromethane (3 mL) at 0° C. under argon was added 1,3-propanedithiol (0.061 g, 0.563 mmol), followed by boron trifluoride etherate (0.07 mL, 0.57 mmol). The resulting mixture was stirred at 0° C. for 1 h and at ambient temperature overnight. The reaction mixture was quenched by pouring into saturated aqueous $Na_2CO_3$, and then extracted with 40% ethyl acetate/hexane. The combined organic layers were dried over anhydrous $MgSO_4$, filtered, and concentrated to afford an oil. Flash chromatography (80% dichloromethane/hexane) yielded the desired dithiane 23 as a white solid (0.175 g, 90%): m.p. 103°–105° C.; $R_f$ 0.2 (50% $CH_2Cl_2$/hexane). The structure of the product was also confirmed using IR, $^1H$ NMR and mass spectroscopy.

(c.) [2-(4,4-Dimethyl-3,4-dihydro-2H-1-benzopyran-6-yl)-2-(4-carboxyphenyl)]-1,3-dithiane (24):

To a suspension of the dithiane 23 (0.145 g, 0.349 mmol) in 75% aqueous methanol (4 mL) was added one pellet of potassium hydroxide (0.106 g). The reaction mixture was stirred at 70° C. for 1 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford a white solid. Recrystallization from dichloromethane-hexane afforded the desired acid 24 as a white powder (0.127 g, 90%): m.p. 204°–205° C. The structure of the product was also confirmed using IR, $^1H$ NMR and mass spectroscopy.

EXAMPLE 9

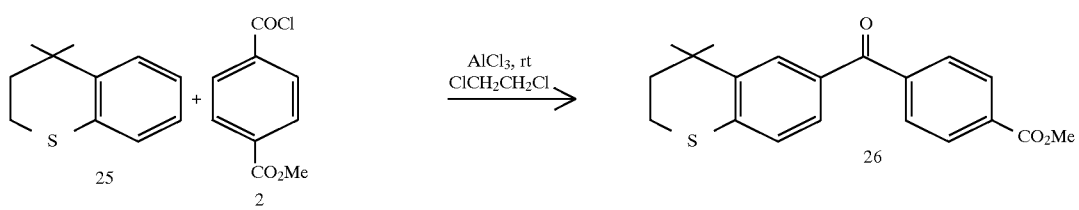

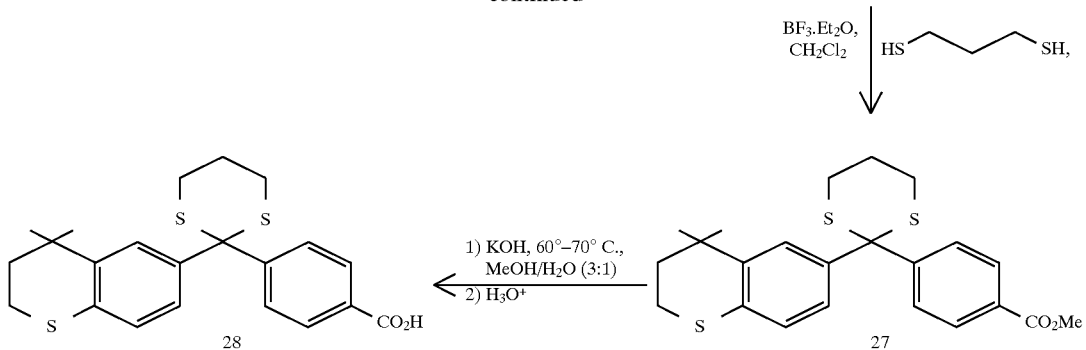

(a.) Methyl 4-[(4,4-dimethyl-3,4-dihydro-2H-1-benzothiopyran-6-yl)carbonyl]benzoate (26):

To a suspension of aluminum chloride (1.65 g, 9.25 mmol) in 1 mL of 1,2-dichloroethane under argon at room temperature was added a solution of 4,4-dimethyl-3,4-dihydro-2H-1-benzothiopyran 25 (1.65 g, 9.25 mmol) (Waugh, K. M., et al., J. Med. Chem. 28:116–124 (1985)) and 4-carbomethoxybenzoyl chloride 2 (1.8 g, 9.06 mmol) in 9 mL of 1,2-dichloroethane. The reaction mixture was stirred overnight and poured onto ice water and extracted with 40% ethyl acetate/hexane. The combined organic layers were washed with saturated aqueous $NaHCO_3$ and brine. The solution was dried over anhydrous $MgSO_4$, filtered and concentrated to afford a green solid (2.1 g). Flash chromatography (80% dichloromethane/hexane) yielded the desired product 26 as a white powder (1.23 g, 40%): m.p. 118°–120° C.; $R_f$ 0.35 ($CH_2Cl_2$). The structure of the product was also confirmed using IR, $^1H$ NMR and mass spectroscopy.

(c.) [2-(4,4-Dimethyl-3,4-dihydro-2H-1-benzothiopyran-6-yl)-2-(4-carboxyphenyl)]-1,3-dithiane (28):

To a suspension of the dithiane 27 (0.1 g, 0.232 mmol) in 75% aqueous methanol (4 mL) was added one pellet of potassium hydroxide (0.12 g). The reaction mixture was stirred at 75° C. for 1 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford a white solid. Recrystallization from dichloromethane/hexane afforded the desired acid 28 as a white powder (0.089 g, 92%): m.p. 211°–212.5° C. The structure of the product was also confirmed using IR, $^1H$ NMR and mass spectroscopy.

EXAMPLE 10

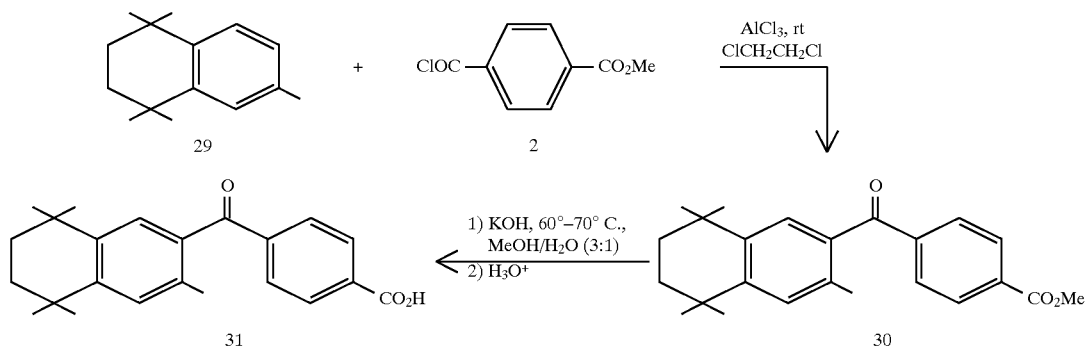

(b.) [2-(4,4-Dimethyl-3,4-dihydro-2H-1-benzothiopyran-6-yl)-2-(4-carbomethoxyphenyl)]-1,3-dithiane (27):

To a solution of the keto-ester 26 (0.12 g, 0.353 mmol) in dichloromethane (3 mL) at 0° C. under argon was added 1,3-propanedithiol (0.06 mL, 0.53 mmol) followed by boron trifluoride etherate (0.07 mL, 0.57 mmol). The resulting mixture was stirred at 0° C. for 1 h and then warmed to room temperature overnight. The reaction mixture was quenched by pouring into saturated aqueous $Na_2CO_3$, and extracted with 40% ethyl acetate/hexane. The combined organic layers were dried over anhydrous $MgSO_4$, filtered, and concentrated to afford an oil. Flash chromatography (80% $CH_2Cl_2$/hexane) yielded the desired dithiane 27 as a white solid (0.145 g, 96%): m.p. 164°–166° C.; $R_f$ 0.27 (50% $CH_2Cl_2$/hexane). The structure of the product was also confirmed using IR, $^1H$ NMR and mass spectroscopy.

(a.) Methyl [4-(5,6,7,8-tetrahydro-3,5,5,8,8-pentamethyl-2-naphthalenyl)carbonyl]benzoate (30):

To a suspension of aluminum chloride (1.10 g, 8.25 mmol) in 30 mL of 1,2-dichloroethane under argon at room temperature was added a solution of 1,2,3,4-tetrahydro-1,1,4,4,6-pentamethylnaphthalene 29 (1.52 g, 7.5 mmol) (Kagechika, H., et al., J. Med. Chem. 31:2182 (1988)) and 4-carbomethoxybenzoyl chloride 2 (1.57 g, 7.87 mmol) in 15 mL of 1,2-dichloroethane. The reaction mixture was stirred overnight and poured onto ice water and extracted with 40% ethyl acetate/hexane. The combined organic layers were washed with saturated aqueous $NaHCO_3$ and brine. The solution was dried over anhydrous $MgSO_4$, filtered and concentrated to afford a brown solid (2.56 g). Flash chromatography (60% dichloromethane/hexane) yielded the desired product 30 as a white, crystalline solid (1.733 g, 64

%): m.p. 146°–149° C.; $R_f$ 0.11 (50% CH$_2$Cl$_2$/hexane). The structure of the product was also confirmed using IR, $^1$H NMR and mass spectroscopy.

(b.) [4-(5,6,7,8-Tetrahydro-3,5,5,8,8-pentamethyl-2-naphthalenyl)carbonyl]benzoic acid (31):

To a suspension of the ester 30 (0.120 g, 0.329 mmol) in 75% aqueous methanol (2 mL) was added potassium hydroxide (0.055 g). The reaction mixture was stirred at 60° C. for 1 h during which time the material dissolved. The solution was cooled to room temperature, acidified with 1N aqueous hydrochloric acid, and then extracted with 80% ethyl acetate/hexane. The combined organic layers were dried over anhydrous MgSO$_4$, filtered, and concentrated to afford a white solid (0.109 g). Recrystallization from benzene/hexane afforded 31 as a white, crystalline solid (0.102 g, 89%): m.p. 209°–212° C. The structure of the product was also confirmed using IR, $^1$H NMR and mass spectroscopy.

(a.) Methyl 4-[1-(5,6,7,8-tetrahydro-3,5,5,8,8-pentamethyl-2-naphthalenyl)-1-ethenyl]benzoate (32):

To a suspension of methyltriphenylphosphonium bromide (0.196 g, 0.55 mmol) in 1 mL of benzene under argon at room temperature was added a 0.5M solution of potassium hexamethyldisilazide in toluene (1.2 mL, 0.6 mmol), and the yellow solution was stirred for 5 min. A solution of keto-ester 30 (0.1 g, 0.274 mmol) in 1.5 mL of benzene was added, and the orange solution was stirred for 3 h at room temperature. The reaction mixture was filtered through a plug of silica gel with 40% ethyl acetate/hexane. The filtrate was concentrated to afford a solid. Flash chromatography (30%; 40% dichloromethane/hexane) yielded the desired product 32 as a white solid (0.077 g, 78%): m.p. 167°–168° C.; $R_f$ 0.4 (50% dichloromethane/hexane). The structure of the product was also confirmed using IR, $^1$H NMR and mass spectroscopy.

(b.) [4-[1-(5,6,7,8-Tetrahydro-3,5,5,8,8-pentamethyl-2-naphthalenyl)-1-ethenyl]benzoic acid (33):

To a suspension of the ester 32 (0.058 g, 0.16 mmol) in 75% aqueous methanol (2 mL) was added one pellet of potassium hydroxide (0.1 g). The mixture was stirred at 70° C. for 1 h during which time the material dissolved. The solution was cooled to room temperature, acidified with 1N aqueous hydrochloric acid, and then extracted with 80% ethyl acetate/hexane. The combined organic layers were dried over anhydrous MgSo$_4$, filtered, and concentrated to afford a white solid. Recrystallization from dichloromethane/hexane afforded the desired acid 33 as a white, crystalline solid (42 mg, 91%): m.p. 230°–231° C. The structure of the product was also confirmed using IR, $^1$H NMR and mass spectroscopy.

EXAMPLE 11

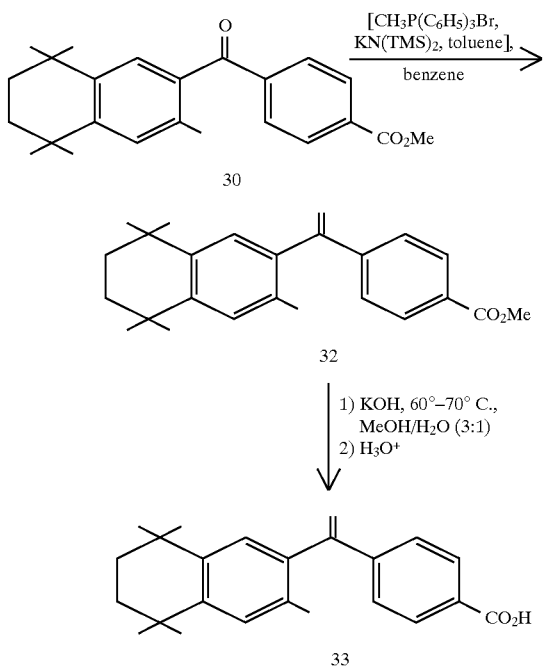

EXAMPLE 12

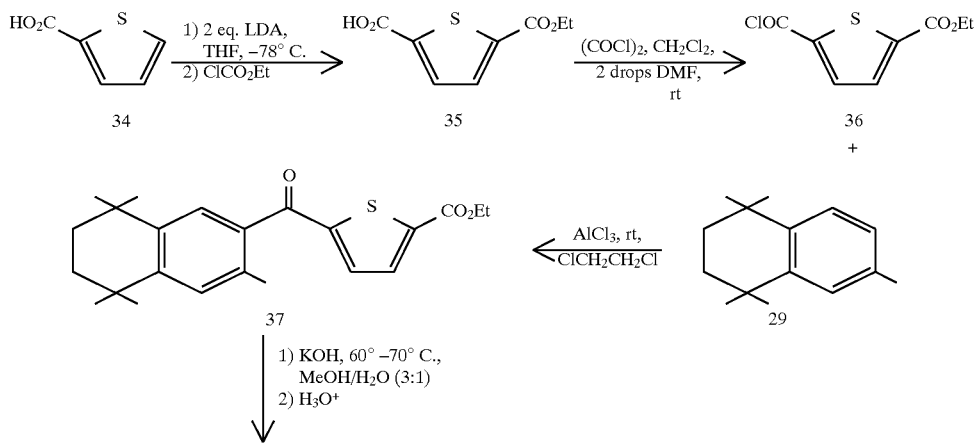

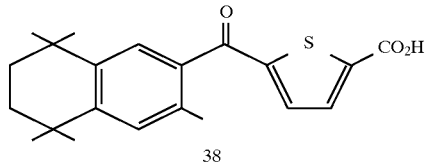

(a.) 5-Carboethoxythiophen-2-carboxylic acid (35):

To a solution of diisopropylamine (3.6 mL, 25.75 mmol) in 10 mL of THF at −78° C. under argon was added a 1.6M solution of n-butyllithium in hexane (16.1 mL, 25.75 mmol). The mixture was stirred for 15 min, and a solution of 2-thiophenecarboxylic acid 34 (1.5 g, 11.705 mmol) (2-thiophenecarboxylic acid 34 is readily available from Aldrich) in 5 mL of THF was added slowly. The mixture was stirred for 15 min, and ethyl chloroformate (2.7 mL, 28.33 mmol) was added. The mixture was stirred for 30 min at −78° C., and warmed to 0° C. for another 30 min. The reaction mixture was poured into saturated aqueous NaHCO$_3$, and washed with 80% ethyl acetate/hexane. The aqueous layer was acidified with acetic acid and extracted with 80% ethyl acetate/hexane. The combined organic layers were dried over anhydrous MgSO$_4$, filtered, and concentrated to afford a yellow solid. Flash chromatography yielded the desired acid 35 (1.76 g, 75%) as a white solid: m.p. >300° C. The structure of the product was also confirmed using IR, $^1$H NMR and mass spectroscopy.

(b.) 5-Carboethoxythiophen-2-carbonyl chloride (36):

To a suspension of acid 35 (0.64 g, 3.2 mmol) in dichloromethane (20 mL) under argon at room temperature was added a 2.0M solution of (COCl)$_2$ in dichloromethane (2.4 mL, 4.8 mmol) and two drops of DMF, and stirred overnight. Excess (COCl)$_2$ and dichloromethane were removed at reduced pressure, and the viscous, light, yellow product was dried overnight to afford the desired benzoyl chloride 36 as a yellow solid. The structure of the product was also confirmed using IR and $^1$H NMR spectroscopy.

(c.) Ethyl 5-[(5,6,7,8-tetrahydro-3,5,5,8,8-pentamethyl-2-naphthalenyl)carbonyl]thiophen-2-carboxylate (37):

To a suspension of aluminum chloride (0.5 g, 3.75 mmol) in 1 mL of 1,2-dichloroethane under argon at room temperature was added a solution of 1,2,3,4-tetrahydro-1,1,4,4,6-pentamethylnaphthalene 29 (0.712 g, 3.52 mmol) and 36 (0.7 g, 3.2 mmol) in 3.5 mL of 1,2-dichloroethane dropwise. The reaction mixture was stirred overnight, and then poured onto ice water, and extracted with 40% ethyl acetate/hexane. The combined organic layers were washed with saturated aqueous NaHCO$_3$ and brine. The solution was dried over anhydrous MgSO$_4$, filtered and concentrated to afford a yellow solid (1.5 g). Flash chromatography (50% dichloromethane/hexane) yielded a light-yellow solid. Recrystallization from dichloromethane/hexane afforded 37 as a white crystalline solid (0.62 g, 50%): m.p. 111°–112° C.; R$_f$ 0.2 (50% CH$_2$Cl$_2$/hexane). The structure of the product was also confirmed using IR, $^1$H NMR and mass spectroscopy.

(d.) 5-[(5,6,7,8-tetrahydro-3,5,5,8,8-pentamethyl-2-naphthalenyl)carbonyl]thiophen-2-carboxylic acid (38):

To a suspension of the ester 37 (50 mg, 0.13 mmol) in 75% aqueous methanol (3 mL) was added one pellet of potassium hydroxide (0.1 g). The reaction mixture was stirred at 70° C. for 1.5 h during which time the material dissolved. The solution was cooled to room temperature, acidified with 1N aqueous hydrochloric acid, and then extracted with 80% ethyl acetate/hexane. The combined organic layers were dried over anhydrous MgsO$_4$, filtered, and concentrated to afford a white solid (46 mg). Recrystallization from methanol afforded the desired acid 38 as a white crystalline solid (42 mg, 91%): m.p. 214°–215° C. The structure of the product was also confirmed using IR, $^1$H NMR and mass spectroscopy.

EXAMPLE 13

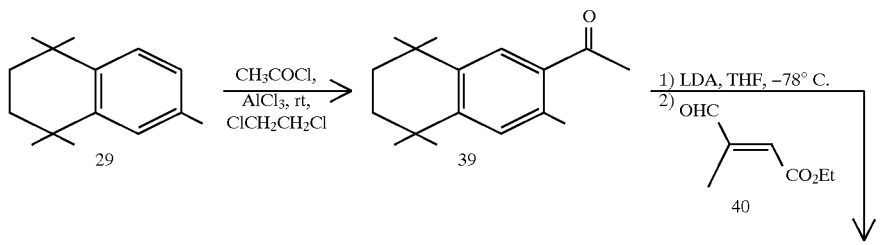

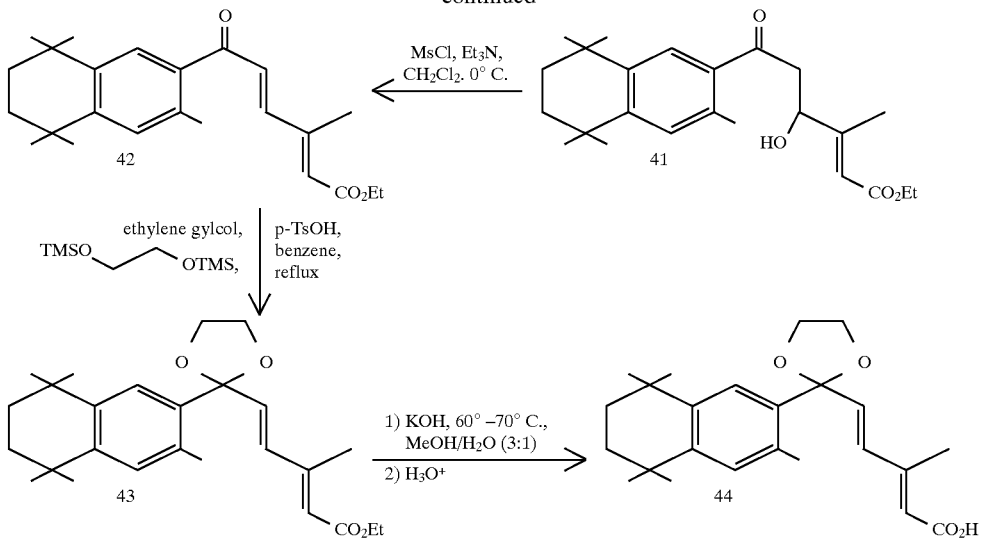

(a.) 2-Acetyl-3,5,5,8,8-pentamethyl-5,6,7,8-tetrahydronaphthalene (39):

To a suspension of aluminum chloride (0.96 g, 7.17 mmol) in 1 mL of 1,2-dichloroethane under argon at room temperature was added a solution of 1,2,3,4-tetrahydro-1,1,4,4,6-pentamethylnaphthalene 29 (1.2 g, 5.93 mmol) and acetyl chloride (0.51 g, 6.52 mmol) in 9 mL of 1,2-dichloroethane. The reaction mixture was stirred for 1 h and then was poured onto ice water and extracted with 40% ethyl acetate/hexane. The combined organic layers were washed with saturated aqueous $NaHCO_3$ and brine. The solution was. dried over anhydrous $MgSO_4$, filtered through a plug of silica gel, and concentrated to afford a white solid 39 (1.45 g, 99%): m.p. 54°–57° C.; $R_f$ 0.62 (10% ethyl acetate/hexane). The structure of the product was also confirmed using IR, $^1H$ NMR and mass spectroscopy.

(b.) Ethyl (E)-4-hydroxy-3-methyl-6-oxo-6-(3,5,5,8,8-pentamethyl-5,6,7,8-tetrahydro-2-naphthalenyl)-2-hexenoate (41):

To a solution of diisopropylamine (0.5 mL, 3.52 mmol) in 7 mL of THF at −78° C. under argon was added a 1.6M solution of n-butyllithium in hexane (2.2 mL, 3.52 mmol). The mixture was stirred for 25 min, and a solution of ketone 39 (0.78 g, 3.2 mmol) in 4 mL of THF was added slowly. The mixture was stirred for 20 min, and a solution of ethyl (E)-3-formyl-2-butenoate 40 (0.45 g, 3.2 mmol) (ethyl (E)-3-formyl-2-butenoate 40 is readily available from Fluka) in 3 mL of THF was added slowly. The mixture was stirred for 35 min at −78° C., poured into saturated aqueous $NH_4Cl$, and extracted with 40% ethyl acetate/hexane. The combined organic layers were dried over anhydrous $MgSO_4$, filtered, and concentrated to afford a light-yellow solid. Flash chromatography yielded the desired alcohol 41 as a white crystalline solid (0.98 g, 80%): m.p. 126°–128° C.; $R_f$ 0.13 (10% ethyl acetate/hexane). The structure of the product was also confirmed using IR, $^1H$ NMR and mass spectroscopy.

(c.) Ethyl (2E,4E)-6-oxo-6-(3,5,5,8,8-pentamethyl-5,6,7,8-tetrahydro-2- naphthalenyl)-2,4-hexadienoate (42):

To a solution of 41 (0.33 g, 0.85 mmol) in 8 mL of THF at 0° C. was added triethylamine (0.5 mL, 4 mmol), and a solution of methylsulfonyl chloride (0.106 g, 0.93 mmol) in 2 mL of THF slowly. The mixture was stirred for 1 h at 0° C. and warmed to room temperature for 30 min. The mixture was filtered through a plug of silica gel with 10% ethyl acetate/hexane. The filtrate was concentrated to afford 42 as a light-yellow solid. Recrystallization from dichloromethane/hexane afforded the desired acid 42 as a yellow powder (0.3 g, 95%): m.p. 101°–102° C.; $R_f$ 0.42 (10% ethyl acetate/hexane). The structure of the product was also confirmed using IR, $^1H$ NMR and mass spectroscopy.

(d.) [2-(5,6,7,8-Tetrahydro-3,5,5,8,8-pentamethyl-2-naphthalenyl)-2-(4-carboethoxy-2E,4E-3-methylbutadienyl)]-1,3-dioxolane (43):

To a solution of keto-ester 42 (0.12 g, 0.33) in 2 mL of benzene was added ethylene gylcol (0.8 mL), 1,2-bis (trimethylsilyloxy)ethane (2 mL) and a catalytic amount of p-TsOH. The reaction mixture was heated at reflux for 2 days and then cooled to room temperature. The solution was poured into saturated aqueous $NaHCO_3$ and extracted with 40% ethyl acetate/hexane. The combined organic layers were dried over anhydrous $MgSO_4$, filtered, and concentrated to afford a solid. Flash chromatography (5% ethyl acetate/hexane) yielded the desired ketal 43 as a colorless oil (0.109 g, 80 %): $R_f$ 0.43 (10% ethyl acetate/hexane). The structure of the product was also confirmed using IR, $^1H$ NMR and mass spectroscopy.

(e.) [2-(5,6,7,8-Tetrahydro-3,5,5,8,8-pentamethyl-2-naphthalenyl)-2-(4-carboxy-2E,4E-3-methylbutadienyl)]-1,3-dioxolane (44):

To a solution of the ester 43 (30 mg, 0.073 mmol) in 75% aqueous methanol (2 mL) was added one pellet of potassium hydroxide (0.1 g). The reaction mixture was stirred at 60° C. for 0.5 h during which time the material dissolved. The solution was cooled to room temperature, acidified with 1N aqueous hydrochloric acid, and then extracted with 80% ethyl acetate/hexane. The combined organic layers were dried over anhydrous $MgSO_4$, filtered, and concentrated to afford a white solid. Recrystallization from dichloromethane/hexane afforded the desired acid 44 as a white, crystalline solid (27 mg, 96 %): m.p. 189°–190° C. The structure of the product was also confirmed using IR, $^1H$ NMR and mass spectroscopy.

EXAMPLE 14

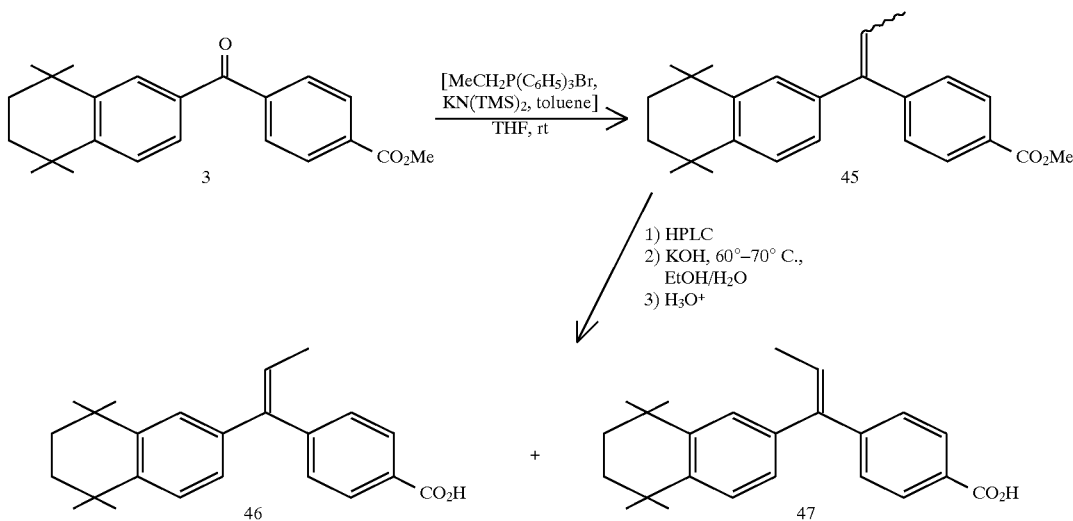

(E) and (Z)-4-[1-(5,6,7,8-Tetrahydro-5,5,8,8-tetramethyl-2-naphthalenyl)propen-1-yl]benzoic acid (46 and 47):

To a suspension of ethyltriphenylphosphonium bromide (160 mg, 0.43 mmol) in 1 mL of THF under argon at 0° C. was added a 0.5M solution of potassium hexamethyldisilazide in toluene (0.95 mL, 0.47 mmol), and the reaction mixture was stirred for 5 min. A solution of keto-ester 3 (100 mg, 0.28 mmol) in 0.8 mL of THF was added, and the orange solution was stirred at room temperature for 3 h. The reaction mixture was diluted with 20% ethyl acetate/hexane and filtered through a plug of silica gel with 20% ethyl acetate/hexane. The solution was concentrated to afford a yellow gum. Chromatography (38% dichloromethane/hexane) yielded the mixture of 45 as a pale-yellow gum (51 mg, 50%): $R_f$ 0.43, 0.47 (40% $CH_2Cl_2$/hexane). Preparative HPLC (Waters Radialpak Novapak silica, 8 mm×10 cm, 2% ether/hexane, 1.0 mL/min, 260 nm) gave a colorless gum 45a (20 mg, $t_r$=9.8 min) and a white solid 45b (25 mg, $t_r$=10.8 min).

To a suspension of the ester 45a (20 mg) in 0.5 mL of ethanol was added a 40% solution of aqueous potassium hydroxide (0.2 g), and the reaction mixture was stirred at 70° C. under argon for 2 h during which time the material dissolved. The solution was then concentrated in an argon stream. The residue was cooled to room temperature, acidified with 1N aqueous sulfuric acid to pH 2–3, and then filtered. The precipitate was repeatedly washed with water (6×1 mL) and dried to afford a white powder (20 mg). Recrystallization from ethyl acetate/hexane afforded the acid 46 as a white powder (16 mg, 16% overall yield): m.p. 212° C. The structure of the product was also confirmed using IR, $^1$H NMR and mass spectroscopy. The regiochemistry of 46 was confirmed by $^1$H nOe NMR spectroscopy.

The ester 45b was hydrolyzed as above to give 25 mg of pale-yellow solid. Recrystallization from ethyl acetate afforded the acid 47 as a pale-yellow powder (21 mg, 20% overall yield): m.p. 229° C. The structure of the product was also confirmed using IR, $^1$H NMR and mass spectroscopy. The regiochemistry of 47 was confirmed by $^1$H nOe NMR spectroscopy.

EXAMPLE 15

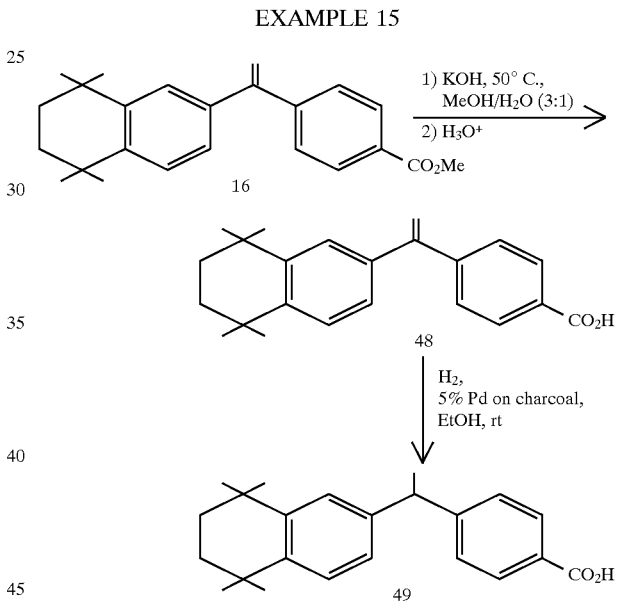

(a.) 4-[1-(5,6,7,8-Tetrahydro-5,5,8,8-tetramethyl-2-naphthalenyl)-1-ethenyl]benzoic acid (48):

To a suspension of the ester 16 (94 mg, 0.27 mmol) in 75% aqueous methanol (2 mL) was added potassium hydroxide (0.045 g), and the reaction mixture was stirred at 50° C. for 14 h during which time the material dissolved. The solution was cooled to room temperature, acidified with 2N aqueous hydrochloric acid, and then extracted with ether. The combined organic layers were washed with water and brine. The organic solution was then dried over anhydrous $MgSO_4$, filtered and concentrated to afford a white solid. Recrystallization from benzene-hexane afforded the desired acid 48 as a white crystalline solid (0.074 g, 82%): m.p. 201°–204° C. The structure of the product was also confirmed using IR, $^1$H NMR and mass spectroscopy.

(b.) 4-[1-(5,6,7,8-Tetrahydro-5,5,8,8-tetramethyl-2-naphthalenyl)-1-ethyl]benzoic acid (49):

The olefin 48 (0.0105 g, 0.0314 mmol) was hydrogenated over 5% palladium on charcoal (1 mg) in 0.5 mL of ethanol at room temperature and atmospheric pressure. After one equivalent (0.7 mL) of hydrogen was taken up, the catalyst was removed by filtration through a small Celite pad. The solvent was removed in vacuo to give the crude acid as a white solid (0.019 g). Recrystallization from benzene-hexane afforded the desired acid 49 as a white crystalline solid (0.0078 g, 74%): m.p. 186°–188° C. The structure of the product was also confirmed using IR, $^1$H NMR and mass spectroscopy.

We claim:

1. A bicyclic aromatic compound having the structural formula

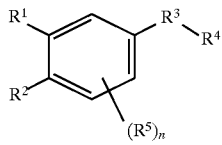

and the pharmaceutically acceptable esters, amides and salts thereof, wherein:

$R^1$ is selected from the group consisting of lower alkyl and adamantyl;

$R^2$ is —O—$R^{13}$ or —S—$R^{13}$ where $R^{13}$ is lower alkyl; or when $R^1$ is ortho to $R^2$, $R^1$ and $R^2$ may be linked together to form a 5- or 6-membered cycloalkylene ring, either unsubstituted or substituted with 1 to 4 lower alkyl groups, and optionally containing 1 or 2 heterocyclic atoms selected from the group consisting of O, S and NR where R is hydrogen or lower alkyl;

$R^3$ is selected from the group consisting of carbonyl,

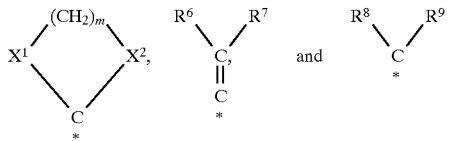

in which $X^1$ and $X^2$ are independently selected from the group consisting of O, S and methylene, wherein at least one of $X^1$ and $X^2$ is O or S, or wherein one of $X^1$ and $X^2$ is NR and the other is methylene, m is 2 or 3, $R^6$, $R^7$, $R^8$ and $R^9$ are independently hydrogen or lower alkyl, or $R^8$ and $R^9$ may be linked together to form a cycloalkylene ring containing 3 to 6 carbon atoms, and * represents the point of attachment of the $R^3$ substituent to the remainder of the molecule;

$R^4$ is selected from the group consisting of

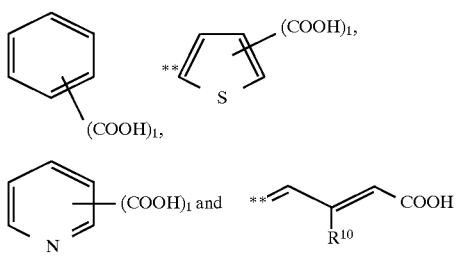

in which $R^{10}$ is hydrogen or methyl, 1 is 0 or 1, and ** represents the point of attachment of the $R^4$ substituent to the remainder of the molecule;

the $R^5$ are independently selected from the group consisting of lower alkyl and lower alkoxy; and n is 0, 1, 2 or 3, with the provisos that: (a) when n is 0, $R^3$ is other than carbonyl, *C=CH$_2$ or CH$_2$; (b) when n is 0, and $R^3$ is

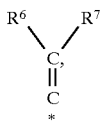

then $R^6$ and $R^7$ are not both hydrogen; (c) when n is 0, and $R^3$ is

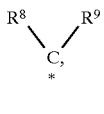

then $R^8$ and $R^9$ are not both hydrogen; (d) when $R^3$ is

in which one of $R^8$ and $R^9$ is hydrogen or lower alkyl and the other is lower alkyl, either (i) $R^1$ and $R^2$ are such that they are not linked together to form a cycloalkyl ring, or (ii) $R^4$ is other than

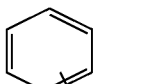

(e) when $R^3$ is

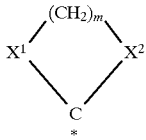

and $X^1$ and $X^2$ are both methylene, $R^4$ is other than

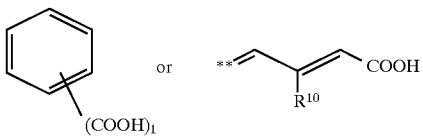

and (f) when $R^3$ is carbonyl,

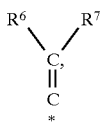

with $R^6$ and $R^7$ being hydrogen, $C_1$ to $C_4$ alkyl, or

with $R^8$ and $R^9$ being hydrogen or $C_1$ to $C_4$ alkyl, and when $R^1$ is ortho to and linked to $R^2$ to form a five-to six-membered cycloalkylene ring

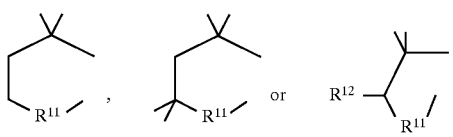

in which $R^{11}$ is O, S, $(CH_3)_2C$, $CH_2$ or NR wherein R is hydrogen or lower alkyl and $R^{12}$ is hydrogen or methyl, then $R^5$ cannot be $C_1$ to $C_4$ alkyl when n is 1 and when $R^5$ is ortho to $R^3$.

2. The compound of claim 1, having a structure selected from the group consisting of

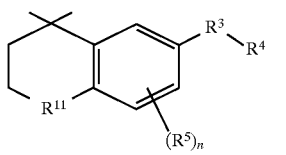 (II)

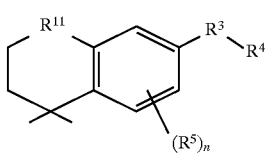 (III)

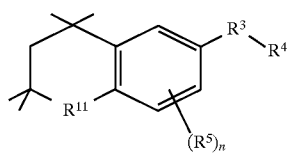 (IV)

and

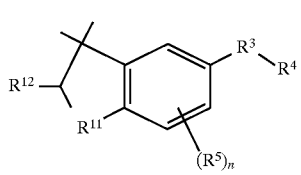 (V)

where $R^{11}$ is selected from the group consisting of O, S, $(CH_3)_2C$ and $CH_2$, and $R^{12}$ is hydrogen or methyl.

3. The compound of claim 2, having the structural formula (II).

4. The compound of claim 3, wherein n is 0.

5. The compound of claim 3, wherein $R^4$ is

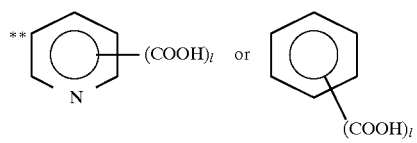

and l is 1.

6. The compound of claim 5, wherein $R^4$ is

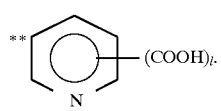

7. The compound of claim 5, wherein $R^4$ is

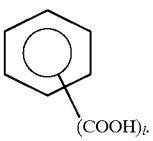

8. The compound of claim 3, wherein $R^3$ has the structural formula

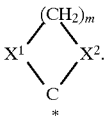

9. The compound of claim 5, wherein $R^3$ has the structural formula

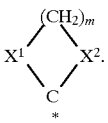

10. The compound of claim 3, wherein $R^3$ has the structural formula

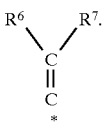

11. The compound of claim 5, wherein $R^3$ has the structural formula

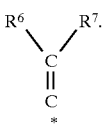

12. The compound of claim 11, wherein $R^3$ is selected from the group consisting of

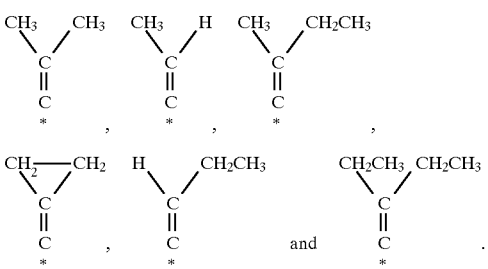

13. The compound of claim 3, wherein $R^3$ has the structural formula

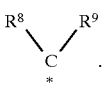

14. The compound of claim 5, wherein $R^3$ has the structural formula

15. The compound of claim 14, wherein $R^3$ is selected from the group consisting of

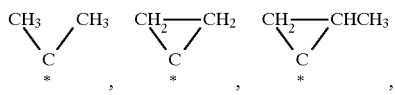

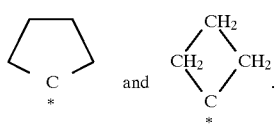

16. The compound of claim 3, having the structural formula

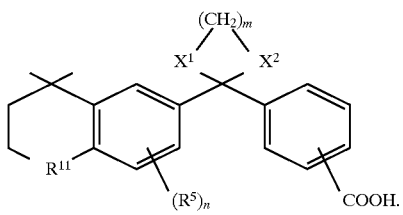

17. The compound of claim 3, having the structural formula

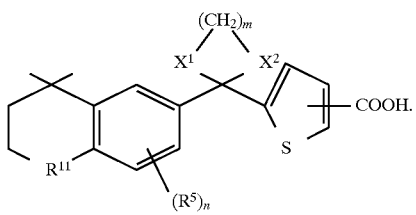

18. The compound of claim 3, having the structural formula

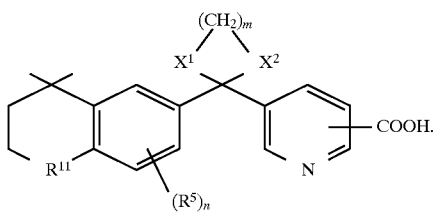

19. The compound of claim 3, having the structural formula

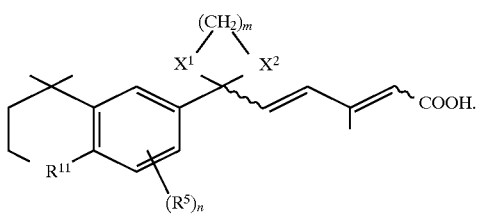

20. The compound of claim 3, having the structural formula

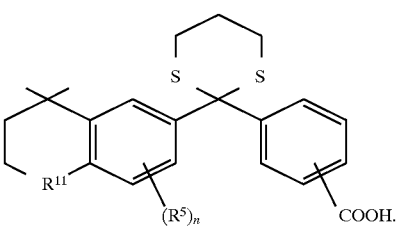

21. The compound of claim 3, having the structural formula

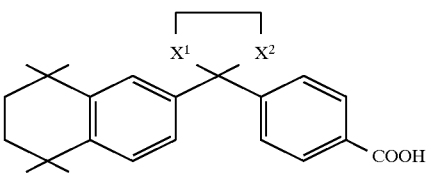

wherein $X^1$ and $X^2$ are independently selected from the group consisting of O and S, or the ammonium salt of the compound.

22. The compound of claim 3, having the structural formula

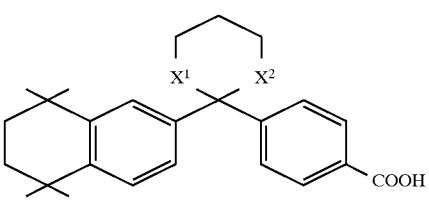

wherein $X^1$ and $X^2$ are independently selected from the group consisting of O and S, or the ammonium salt of the compound.

23. The compound of claim 3, having the structural formula

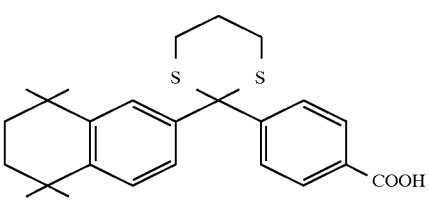

wherein $R^1$ is O or S.

24. The compound of claim 3, having the structural formula

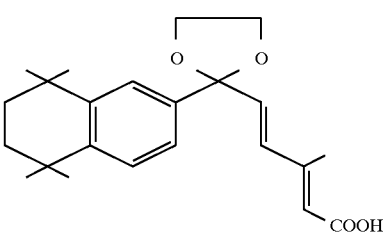

and the ammonium salt of the compound.

25. The compound of claim 3, having the structural formula

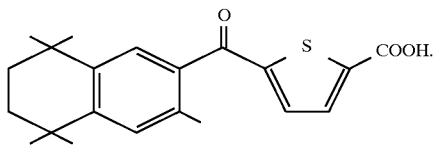

26. A pharmaceutical composition for control of cellular processes regulated by retinoic acid, vitamin D, or thyroid hormone, comprising an effective regulating amount of the compound of claim 1 in combination with a pharmaceutically acceptable carrier.

27. A pharmaceutical composition for control of cellular processes regulated by retinoic acid, vitamin D, or thyroid hormone, comprising an effective regulating amount of the compound of claim 3 in combination with a pharmaceutically acceptable carrier.

28. A method for treating an individual afflicted with a disease caused by malfunction of cell differentiation processes regulated by retinoids, thyroid hormone, vitamin D, or 9-cis-retinoic acid, comprising administering to the individual a therapeutically effective amount of the compound of claim 1 or a pharmaceutical composition thereof.

29. A method for treating an individual afflicted with a disease caused by malfunction of cell differentiation processes regulated by retinoids, thyroid hormone, vitamin D, or 9-cis-retinoic acid, comprising administering to the individual a therapeutically effective amount of the compound of claim 3 or a pharmaceutical composition thereof.

30. The compound of claim 21, wherein $X^1$ and $X^2$ are both O.

31. A pharmaceutical composition for control of cellular processes regulated by retinoic acid, vitamin D, or thyroid hormone, comprising an effective regulating amount of the compound of claim 30 in combination with a pharmaceutically acceptable carrier.

32. A method for treating an individual afflicted with a disease caused by malfunction of cell differentiation processes regulated by retinoids, thyroid hormone, or vitamin D, comprising administering to the individual a therapeutically effective amount of the compound of claim 30, or a pharmaceutical composition thereof.

* * * * *

Disclaimer

5,837,725—Marcia I. Dawson, Menlo Park, CA; James F. Cameron, Palo Alto, CA; Peter D. Hobbs, Moss Beach, CA; Ling Jong, Sunnyvale, CA; Magnus Pfahl, Solana Beach, CA; Xiao-kun Zhang, La Jolla, CA; Jürgen M. Lehmann, Solana Beach, CA. BRIDGED BICYCLIC AROMATIC COMPOUNDS AND THEIR USE IN MODULATING GENE EXPRESSION OF RETINOID RECEPTORS. Patented November 17, 1998. Disclaimer filed March 16, 2005, by the inventor, Marcia I. Dawson.

Hereby enters this disclaimer to claims 26-29 of said patent.

*(Official Gazette, November 1, 2005)*